(12) United States Patent
Carle et al.

(10) Patent No.: US 6,300,370 B1
(45) Date of Patent: *Oct. 9, 2001

(54) CAMOMILE OILS HAVING A HIGH CONTENT OF NATURAL POLY-YNES AND PROCESS FOR THEIR PREPARATION

(75) Inventors: Reinhold Carle, Rodermark; Otto Isaac, Hanau, both of (DE)

(73) Assignee: ASTA Medica Aktiengesellschaft (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/095,146

(22) Filed: Jun. 10, 1998

Related U.S. Application Data

(63) Continuation-in-part of application No. 07/908,856, filed on Jul. 1, 1992, now Pat. No. 5,902,587, which is a continuation of application No. 07/780,387, filed on Oct. 23, 1991, now abandoned, which is a continuation of application No. 07/155,555, filed on Feb. 12, 1998, now abandoned.

(30) Foreign Application Priority Data

Feb. 13, 1987 (DE) .................................................. 37 04 519

(51) Int. Cl.$^7$ .................................................. A61K 35/78
(52) U.S. Cl. ........................ 514/464; 514/462; 424/725; 424/778
(58) Field of Search ..................................... 514/462, 464; 424/195.1, 725, 778

(56) References Cited

U.S. PATENT DOCUMENTS

| 4,786,497 | 11/1988 | Issac et al. ........................ 424/764 |
| 4,786,498 | 11/1988 | Issac et al. ........................ 424/764 |
| 5,902,587 | * 5/1999 | Carle et al. ...................... 424/195.1 |

FOREIGN PATENT DOCUMENTS

| 362 056 | 4/1981 | (AT) . |
| 24 02 802 | 7/1975 | (DE) . |
| 24 34 338 | 1/1976 | (DE) . |
| 154 872 | 9/1985 | (EP) . |
| 1 560 371 | 2/1980 | (GB) . |
| 2 167 955 | 6/1986 | (GB) . |
| 2 170 404 | 8/1986 | (GB) . |

OTHER PUBLICATIONS

Jerzmanowska, "Plant Substances—Methods of Isolation," 1967, pp. 11, 16 and 36.
H. Schilcher, "Die Kamille," Wiss. Verlagsges.Stuttgart, 1987, p. 86.
Auterhoff et al., "Deutsche Apotheker–Zeitung," Neues aus der Pharmazeutischen Biologie, Jan. 15, 1976, pp. 45–50.

* cited by examiner

*Primary Examiner*—Jean C. Witz
(74) *Attorney, Agent, or Firm*—Venable; Ann S. Hobbs

(57) ABSTRACT

Camomile oil having a high cis- and trans-spiroether content is produced in a process which includes steam distillation or aqueous distillation of fresh camomile or an extraction residue of camomile.

15 Claims, No Drawings

US 6,300,370 B1

CAMOMILE OILS HAVING A HIGH CONTENT OF NATURAL POLY-YNES AND PROCESS FOR THEIR PREPARATION

CROSS REFERENCE TO RELATED APPLICATIONS

This application is a continuation-in-part of U.S. application Ser. No. 07/908,856, filed Jul. 1, 1992, U.S. Pat. No. 5,902,587, which is a continuation of application Ser. No. 07/780,387, filed Oct. 23, 1991, abandoned, which is a continuation of application Ser. No. 07/155,555, filed Feb. 12, 1988, abandoned, which claims the priority of application no. P3704519.9, filed Feb. 13, 1987 in Germany, the contents of these applications being incorporated herein by reference in their entirety.

BACKGROUND OF THE INVENTION

1. Field of the Invention

The present invention relates to camomile oil having a high content of natural cis- and trans-spiroethers and to a method for its preparation.

2. Background Information

Camomile (*Chamomilla recutita* Rauschert (syn. *Matricaria chamomilla* (L.)) is used as such or in the form of various preparations. The activity of camomile is attributed to hydrophilic active ingredients such as flavones and polysaccharides and to lipophilic active ingredients which are components of essential camomile oil.

Lipophilic camomile active ingredients that are of importance in assessing the quality of camomile and of camomile extracts are, in addition to (−)-α-bisabolol and chamazulene, poly-ynes such as cis- and trans-ene-yne-dicycloether (=spiroether). The spiroethers of camomile have anti-inflammatory and spasmolytic properties. These spiroethers are, however, easily decomposed, especially at slightly elevated temperatures.

Cis-ene-yne-dicycloether (also known as cis-spiroether) has the following structure:

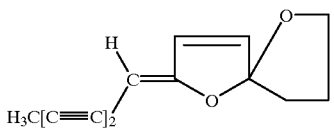

Trans-ene-yne-dicycloether (trans-spiroether) has the following structure:

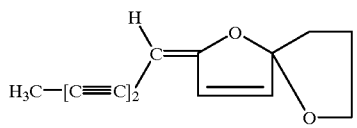

Essential camomile oil can either be obtained by distillation or by extraction of camomile materials, normally dried camomile heads.

Whereas distillation enables an almost complete extraction of the other components of the essential oil, the therapeutically important thermolabile spiroethers are, however, largely decomposed by this process. The oil obtained by distillation consequently no longer displays the active ingredient profile which is characteristic of camomile. On the other hand, it is not possible to obtain the essential oil of camomile completely by extraction. Thus, for example, in the manufacture of fluid extracts with 45% ethanol, only about half of the bisabolol and chamazulene-containing oils contained in the product are recovered in the extract with the sensitive spiroethers.

SUMMARY OF THE INVENTION

In accordance with the present invention, it has now surprisingly been found that by means of steam distillation of camomile extract residues (residues of extractions, dried or deep frozen, of fresh camomile) or of fresh camomile flowers (fresh camomile), camomile oils are obtained which, despite the heat treatment, display high contents of poly-ynes, i.e. in particular high contents of thermolabile cis- and/or trans-ene-yne-dicycloethers.

For aqueous distillation or steam distillation, preferred parts of the camomile plant are camomile flowers and stalks (see Chamomile Oil, German Type: Food Chemical Codex, Fourth Edition, page 98, National Academic Press, Washington, D.C., 1996). For extraction, preferred parts of camomile plant are camomile flowers (only with stalks residues not exceeding a length of 10 to 200 mm) (see German Pharmacopoia, 9th edition, Frankfurt, Germany, 1986, pages 937–939).

The above-mentioned extraction of fresh, dried or deep-frozen camomile flowers is preferably carried out by using an aqueous organic solvent, such as an aqueous $C_1$–$C_6$ alkanol such as methanol, ethanol, isopropanol or aqueous acetone. The water content is preferably not less than 20% (v/v).

The process of the invention therefore makes it possible for the first time to manufacture camomile oil having a high content of natural spiroethers. Such camomile oil is, for example, suitable as an additive to aqueous-alcoholic camomile extracts in order to standardize these to a high content of essential oil with the lipophilic camomile active ingredients, with the typical active ingredient profile of camomile retained.

In addition, the process of the invention makes it possible to economically utilize residues from camomile extraction since the essential oil still present in the extraction residues of the camomile product or of fresh camomile is recovered with a high content of natural spiroethers. Apart from the improved yield of active ingredient, this leads to considerable savings in the cost of raw materials for the manufacture of extracts.

It is not only the use of expensive drying installations which is rendered superfluous in the distillation of extraction residues of fresh camomile flowers or of unprocessed fresh camomile flowers. The appreciable running costs for the conventional preparation of the material to be distilled through drying are also avoided. In this manner it is possible to considerably reduce the cost of the manufacture of extraction preparations.

The addition of camomile oils obtained according to the invention having a high content of spiroethers also yields extracts having an active ingredient profile typical for camomile when mixed with camomile oils conventionally distilled from camomile produce in the manufacture of camomile extract preparations.

The extraction of the oils according to the invention is carried out by means of steam distillation or aqueous distillation.

In the case of steam distillation, superheated steam is introduced into a distillation vessel. The superheated steam can be under normal pressure or under an overpressure of up to 4–5 bar. For example the superheated steam may be under a pressure of 0–1, preferably 0–0.5 bar. The temperature of the superheated steam is, for example, between 100 to 140° C. (maximum 145° C.), preferably 100 to 130° C., in particular 105 to 115° C.

The duration of distillation is, for example, 2–10 hours, preferably 2–4 hours. No additives are added to the material to be distilled during steam distillation. The distillation may be performed continuously or discontinuously.

Aqueous distillation is carried out by heating a distillation vessel charged with water (temperature for example 100° C.). In so doing, one part by weight of the material to be distilled is added to at least one part by weight of water, preferably to 10–100 parts by weight, in particular to 10–60 parts by weight of water which may contain conventional additives such as reducing agents (for example sodium ascorbate, ascorbic acid) as well as mineral acids (such as hydrochloric acid, sulphuric acid) or alkali hydroxides (such as dilute NaOH) to adjust the pH.

Distillation may be effected at pH values between 4–8; adjustment of the pH is preferably avoided so that distillation takes place at neutral pH. Aqueous distillation is completed after 1–4 hours, preferably after 2–3 hours.

The amount of reducing agents added is, for example, 0.1 to 1 part by weight based on 1 part by weight of plant material.

In order to carry out distillation the material to be distilled may be well crushed. The moisture content of the material to be distilled, for example when using residues from camomile extraction, is on average 60% (water-alcohol) and on average 80% (water) when using fresh camomile.

Distillation may be carried out in conventional mobile or stationary distillation vessels.

The distillate condensed by cooling is for example collected in a device (vessel) which enables a phase separation of the essential camomile oil and water on the basis of the different specific gravities (for example a Florentine receiver, but also other conventional separators may be used).

The essential camomile oil of the upper phase can, for example, be used, after separation of the aqueous phase without further purification, for the manufacture of camomile extract preparations. The phase separation may be, for example, be facilitated by addition of salts (for example NaCl) (salting out).

In the case of aqueous distillation the distillation apparatus may optionally be flushed once or several times (2 to 3 times) after completion of the distillation with a low-boiling lipophilic solvent, for example with a saturated liquid aliphatic hydrocarbon having 5 to 7 carbon atoms (for example n-pentane, petroleum ether). This flushing serves to remove the last oil residues from the distillation bridge. 1 to 2 parts by weight of hydrocarbon per 1 part by weight dry weight of the extraction residue used may, for example, be used for flushing purposes. After removal of the hydrocarbon (see below) the residue is combined with the camomile oil of the aqueous distillate.

Should the hydrocarbon be combined with the aqueous distillate, the active ingredients of the distillate pass into the hydrocarbon. Separation of the hydrocarbon phase from the aqueous phase is then effected, for example, in known manner by addition of NaCl (salting-out) followed by repeated shaking out (for example twice) of the aqueous phase with the hydrocarbon. Following drying of the hydrocarbon phase, the camomile oil is obtained by removal of the hydrocarbon, expediently at temperatures between 40 and 60° C. The final hydrocarbon residues may, for example, be removed by means of a hot air steam (temperature 40 to 60° C.).

By "fresh camomile flowers" is meant camomile flowers which are distilled within 24 hours of picking or frozen within this period.

The process of the invention may be applied on a general basis, in other words it is suitable for all varieties of camomile containing spiroether. The following camomiles (or the products prepared therefrom) are in particular used: the diploid variety of camomile Degumill (DDR-Sortenschutzrecht Degumill; German Patent 24 02 802; Italian Patent 1 035 096), the tetraploid variety of camomile Manzana (German Offenlegungsschrift 34 23 207), and tetraploid camomile according to German Offenlegungsschrift 35 42 756.

Furthermore the following diploid forms of camomile may for example be used as starting material: "Camomile of Argentinian provenance" (see L. Z. Padula, R. V. D. Rondina and J. D. Coussio, Quantitative Determination of Essential Oil. Total Azulenes and Chamazulene in German Chamomile, *Matricaria chamomilla,* Cultivated in Argentina; Planta med. 30, 273–280, 1976) as well as all camomiles which display clearly measurable concentrations of (–)-α-bisabolol (generally more than 5% of the essential oil) in the essential oil. For example those diploid camomiles may be considered which are described in the following literature references: Schilcher, H., "Neuere Erkenntnisse bei der Qualitaetsbeurteilung von Kamillenoel beziehungsweise Kamillenblueten", Panta med. 23, 132–144 (1973); Motl, O., M. Felkova, V. Lukes & M. Jasicova "Zur gaschromatographischen Analyse und zu chemischen Typen von Kamillenoel", Arch. Pharm. 310, 210–215 (1977); Franz, Ch., J. Hoelzl & A. Voemel "Preliminary Morphological and Chemical Characterization of some Populations and Varieties of *Matricaria chamomilla* L.,", Acta Hort. 73, 109–114 (1978).

The following tetraploid starting camomiles may, for example, also be considered as the starting material: the camomile varieties Bodegold (DDR), Pohorelicky (CSSR), Zloty Lan (Poland), BK-2 (Hungary). These varieties are described in the following literature references: M. Chladek, V. Kosova, K. Hruby, Pharmazie 13, 712–718 (1958); W. Czabajska, Diss. Posnan (1963); W. Poethke and P. Bulin, Pharm. Zhalle 108, 813–823 (1969); I. Sarkany, Herb. Hungar. 4 (1), 125–169 (1965).

Camomile extract residues which may be used for the process of the invention may for example be such residues which are quite generally obtained during conventional extraction of camomile products or of fresh camomile with alcohols or with alcohol-water mixtures. The alcohols used for such extractions may, for example, be the following alcohols and their mixtures with water: straight or branched aliphatic alcohols with 1–6 carbon atoms as well as also solketal (2,2-dimethyl-4-hydroxymethyl-1,3-dioxolane), such as, for example, methanol, ethanol, propan-1-ol, propan-2-ol, butanol and similar alcohols. It is also possible to use mixtures of these solvents as well as mixtures with water. In the case of aqueous mixtures the water content is, for example, 0 to 65, preferably 20 to 60, in particular 30 to 55 percent by volume (volume for volume).

The camomile extraction residues may be subjected to the distillation of the invention immediately, i.e., when still in a damp condition.

It is, however, also possible to dry these residues (conditions: 40–60° C., 2–5 hours) and optionally process them further according to the invention after storage (conditions: 15–25° C., relative humidity: 40–50%) and transport.

The camomile oil obtained according to the invention contains at least 1 percent by weight, preferably at least 1.5 percent, in particular at least 2 percent by weight of poly-ynes (sum of all poly-ynes). For example the poly-yne content (sum of all poly-ynes, i.e. natural poly-ynes) is 2 to 20, preferably 4 to 18, in particular 10 to 15 percent by weight. The cis-spiroether content is, for example, at least 1 percent by weight, preferably 2 to 18 percent, in particular 5 to 15 percent by weight. The trans-spiroether content is, for example, at least 0.5, preferably 0.5 to 15, in particular 1 to 10 percent by weight. The chamazulene content lies, for example, between 0.9 and 8 percent by weight, preferably between 3 and 6 percent by weight. The α-bisabolol content lies, for example, between 5 and 30 percent by weight, preferably between 22 and 32 percent by weight. The bisabolol oxide A content lies, for example, between 1 and 10 percent by weight, preferably between 2 and 4 percent by weight. The bisabolol oxide B content lies, for example, between 0.8 and 15 percent by weight, preferably between 2 and 4 percent by weight.

The camomile oil obtained according to the invention is for example added with mixing in pure form or as a solution in a physiologically acceptable solvent (for example ethanol) to aqueous-alcoholic camomile extracts obtained in known manner. In the case of the aqueous-alcoholic extracts there are meant, for example, those manufactured using ethanol or isopropanol. The alcohol content should not be less than 20 percent by weight. In general the alcohol content of the extract should be 20 to 55, preferably 20 to 50 percent by weight, in particular 20 to 40 percent by weight. The addition of the camomile oil of the invention to such extracts should be so calculated that the end product has an essential oil content of 100–250 mg per 100 g, preferably 180–200 mg per 100 g of alcoholic and/or aqueous-alcoholic extract. The bisabolol content is then, for example with the use of a camomile rich in bisabolol, 20–100 mg per 100 g, preferably 40–80 mg per 100 g of extract. The extract then contains, for example, 1.5 mg per 100 g of cis- and trans-spiroether.

Camomile extracts or camomile extract preparations obtained by addition of the camomile oil of the invention contain, for example: at least 100 mg per 100 g of poly-ynes, preferably 1 to 10, in particular 2 to 5 mg per 100 g. The cis-spiroether content is at least 0.5 mg per 100 g, preferably 0.7 to 4.0 in particular 1.0 to 3.0 mg per 100 g. The trans-spiroether content is at least 0.3, preferably 0.7 to 3.0, in particular 0.7 to 1.4 mg per 100 g. The chamzulene content lies, for example, between 3 and 25 mg per 100 g, preferably between 3 and 20, in particular between 3 and 18 mg per 100 g. The a-bisabolol content lies, for example, between 30 and 80, in particular between 40 and 60 mg per 100 g. The bisabolol oxide A content lies, for example, between 5 and 30 mg per 100 g, preferably between 5 and 25, in particular between 5 and 20 mg per 100 g. The bisabolol oxide B content lies, for example between 3 and 20 mg per 100 g, preferably between 3 and 18, in particular between 3 and 15 mg per 100 g.

DETAILED DESCRIPTION OF PREFERRED EMBODIMENTS

Example 1

41 g of camomile extract residue[1] (corresponding to 10 g of dry weight) are mixed with 500 ml of water in a 1000 ml round-bottom flask, the mixture is adjusted to pH 6.5 with dilute sodium hydroxide solution and distillation for about 3 hours. The collection vessel may, for example, be a vibrating flask of 1000 ml capacity. After 400 ml of distillate have been obtained, distillation is continued without cooling for about 2 more minutes. The distillation bridge and condenser are then flushed with 80 ml of pentane. The pentane is combined with the distillate and shaken out with 65 g of sodium chloride. The extraction process is repeated twice more with, in each case, 80 ml of pentane. The combined organic phases are dried over 8 g of anhydrous sodium sulfate and filtered. The receiver and filer are washed again twice with, in each case, 10 ml of pentane and the pentane phase is subsequently concentrated under mild conditions to about 5 ml (water bath 50° C., rotary evaporator). The rest of the pentane is distilled off using a hot air stream (temperature: 50–60° C., fan).

[1]This is the camomile residue of a camomile extract obtained using ethanol-water (47:53 volume for volume). The camomile product used was a product rich in bisabolol which had been prepared according to German patent specification 24 02 802 from the Degumill variety of camomile.

A camomile oil was obtained having the following composition:

| | |
|---|---|
| chamazulene | 3.6% |
| (-)α-bisabolol | 20.5% |
| bisabolol oxide A | 2.7% |
| bisabolol oxide B | 4.1% |
| cis-spiroether | 10.2% |
| trans-spiroether | 1.7%. |

Comparative Example (Known Process)

10 g of dried camomile flowers (the product is similar to the camomile product used in Example 1 prior to extraction) is distilled as described in Example 1.

The distilled oil has the following composition:

| | |
|---|---|
| chamazulene | 7.6% |
| (-)-α-bisabolol | 24.4% |
| bisabolol oxide A | 1.6% |
| bisabolol oxide B | 1.7% |
| cis-spiroether | 0.2% |
| trans-spiroether | not found. |

Example 2

37.8 g of fresh camomile rich in bisabolol of the Degumill variety of camomile (corresponding to 10 g of the product, that is dried camomile flowers) is introduced into a 1000 ml two-necked flask. Following setting up of the distillation bridge with pellet condenser, steam is introduced from one side from a steam generator. Distillation is interrupted after 4 hours.

The distilled essential oil of the upper phase is separated using a Florentine receiver and the composition of the oil analyzed.

| | |
|---|---|
| chamazulene | 12.5% |
| (-)-α-bisabolol | 22.1% |
| bisabolol oxide A | 4.7% |
| bisabolol oxide B | 3.4% |

-continued

| | |
|---|---|
| cis-spiroether | 11.8% |
| trans-spiroether | 7.3%. |

Comparative Example (Known Process)

10 g of dried camomile flowers (the product is identical to the carefully dried camomile used in Example 2) is distilled as described in Example 2.

The camomile oil separated out from the upper phase has the following composition:

| | |
|---|---|
| chamazulene | 9.6% |
| (-)-α-bisabolol | 21.2% |
| bisabolol oxide A | 3.0% |
| bisabolol oxide B | 3.9% |
| cis-spiroether | 1.2% |
| trans-spiroether | 0.5%. |

Process Example 3

Process Example 3: (Extraction residue with a high ethanol content of 10–25% w/w, preferably 13–20% w/w)

Preparation of the chamomile extraction residue:

400 kg of dried plant material[2] was extracted by moved maceration using about 2100 kg of aqueous ethanol (37.6% w/w) which contained sodium acetate, sodium ascorbate and sodium hydroxide as additives. One effect of the additives is to improve the stability of camazulene and to improve the solubility of flavones in the aqueous extract.

[2] The camomile plant material used was a mixture of camomile rich varieties of camomile named DEGUMIL, MANZANA I and MANZANA II which had been prepared according to the German patent specifications 24 02 802, 34 23 207 and 35 42 756, respectively.

After 1 hour the extraction mixture was filtered off at a pressure of 3–5 bar thereby yielding about 1,800 kg of the liquid extract and about 700 kg of extraction residue ("draff"). The obtained draff contained about 15% (w/w) of pure ethanol.

Prior to the present invention an extraction residue as described above had either to be subjected to combustion or to be handled as separate waste.

The obtained extraction residue can be stored for several weeks, such as 6 weeks or longer.

Distillation of an Extraction Residue Containing a High Ethanol Content

Distillation was performed by a modified continuous process as described by R. Carle and G. Fiedler in *G. Pharm. Ind.* 52, 9, pages 1142–1146 (1990).

Two modifications of the process by Carle and Fiedler have been elaborated, since due to the high ethanol content in the extraction residue, separation of the camomile oil phase (upper phase) from the water phase (lower phase) at the condenser site was prevented or hindered.

Due to the remaining additives, the pH value of the extraction residue is between 4 to 8.

Modification A (2-step distillation):

6,200 kg of the extraction residue were distilled within 3.8 hours:
Steam velocity: 345 kg/h
Amount of extraction residue per hour: 1619 kg/h
Steam/residue-ratio: 1:4–6, preferably 1:4.7
Ethanol content in the aqueous distillate: 42% w/w Subsequently, 3,150 kg of the ethanol free extraction residue were distilled within 5 hours:
Steam velocity: 650 kg/h
Amount of extraction residue per hour: 530 kg/h
Steam/residue-ratio: 1.1–1.3:1
Yield: 2.9 l per day (=within 5 hours)
Analysis of the essential oil:

| | |
|---|---|
| bisabolol | 17.7% |
| camazulene | 1.2% |
| cis-spiroether | 2.4% |
| trans-spiroether | 0.7% |

Modification B (1-step distillation):

Distillation of the extraction residue with a high ethanol content (15% w/w) was carried out within 8.42 hours by using a high steam/residue-ratio:
Steam velocity: 680 kg/h
Amount of extraction residue per hour: 500 kg/h
Steam/residue ratio: >1.3–2.0:1, preferably ≧1.38–2:1
Ethanol content in the aqueous phase of the distillate: <10% w/w
Yield: 7.3 l of essential oil per day (=within 8.42 hours)
Analysis of the essential oil:

| | |
|---|---|
| bisabolol | 19.2% |
| camazulene | 2.3% |
| cis-spiroether | 3.8% |
| trans-spiroether | 0.4% |

What is claimed is:

1. A process for manufacturing essential camomile oil having a high content of natural spiroethers, said process comprising subjecting a camomile extraction residue to steam distillation or to aqueous distillation to obtain an essential camomile oil having a cis-spiroether content of at least 0.5 mg per 100 g of camomile oil and a trans-spiroether content of at least 0.3 mg per 100 g of camomile oil, said camomile extraction residue having been prepared by subjecting fresh, dried or deep frozen camomile flowers and stalks to treatment with an aqueous or organic solvent or a mixture thereof.

2. The process according to claim 1 wherein said aqueous solvent is an alcohol-water mixture.

3. A process for the manufacture of camomile oil having a high content of natural spiroethers, said process comprising the steps of
   a. subjecting fresh, dried or deep-frozen camomile flowers and stalks, *Matricaria Chamomilla* (L.), to extraction by using a solvent selected from the group consisting of alcohol, an alcohol-water mixture, and mixtures thereof to obtain a liquid extract and a residue;
   b. separating the liquid extract from the residue; and
   c. subjecting the residue to steam distillation or to aqueous distillation to obtain a distillate;
   d. separating the camomile from the distillate by phase separation, or by extraction with an organic solvent and subsequent evaporation of the solvent, to obtain a camomile oil with a cis-spiroether content of at least 0.5 mg per 100 g of camomile oil and a trans-spiroether content of at least 0.3 mg per 100 g of the camomile oil.

4. The process according to claim 3 in which the residue is subjected to an aqueous distillation and the aqueous distillation is conducted at a pH value between 4 and 8.

5. The process according to claim 4 in which a reducing agent is present during the aqueous distillation.

6. The process according to claim 5 in which the reducing agent is selected from the group consisting of ascorbic acid and sodium ascorbate.

7. The process according to claim 3 in which the residue is subjected to steam distillation at a steam temperature of up to 145° C.

8. The process according to claim 3 in which the residue is subjected to steam distillation at a steam pressure of up to 5 bar.

9. A process for the manufacture of camomile oil having a high content of natural spiroethers including a cis-spiroether content of at least 0.5 mg per 100 g of camomile oil and a trans-spiroether content of at least 0.3 mg per 100 g of the camomile oil, which process comprises subjecting fresh camomile, *Matricaria Chamomilla* (L.), or an extraction residue of a camomile extraction to steam distillation or to aqueous distillation.

10. The process according to claim 9 in which the fresh camomile or said extraction residue of a camomile extraction is subjected to an aqueous distillation and the aqueous distillation is conducted at a pH value between 4 and 8.

11. The process according claim 10 in which a reducing substance is present during the aqueous distillation.

12. The process according to claim 11 in which the reducing agent is selected from the group consisting of ascorbic acid and sodium ascorbate.

13. The process according to claim 9 in which the fresh camomile or said extraction residue of a camomile extraction is subjected to steam distillation at a temperature up to 145° C.

14. The process according to claim 9 in which the fresh camomile or said extraction residue of a camomile extraction is subjected to steam distillation at a pressure up to 5 bar.

15. The process according to claim 1 wherein said alcohol is selected from the group consisting of methanol, ethanol, propan-1-ol, propan-2-ol and butanol.

* * * * *